United States Patent
Yang et al.

(10) Patent No.: US 12,121,358 B2
(45) Date of Patent: Oct. 22, 2024

(54) SIGNAL PROCESSING SYSTEM FOR BRAIN MACHINE INTERFACE AND METHOD PERFORMED BY THE SYSTEM

(71) Applicant: AGENCY FOR SCIENCE, TECHNOLOGY, AND RESEARCH, Singapore (SG)

(72) Inventors: Huijuan Yang, Singapore (SG); Cuntai Guan, Singapore (SG); Haihong Zhang, Singapore (SG); Kai Keng Ang, Singapore (SG); Rosa Qi Yue So, Singapore (SG)

(73) Assignee: AGENCY FOR SCIENCE, TECHNOLOGY, AND RESEARCH, Singapore (SG)

( * ) Notice: Subject to any disclaimer, the term of this patent is extended or adjusted under 35 U.S.C. 154(b) by 1031 days.

(21) Appl. No.: 17/050,284

(22) PCT Filed: Apr. 29, 2019

(86) PCT No.: PCT/SG2019/050236
§ 371 (c)(1),
(2) Date: Oct. 23, 2020

(87) PCT Pub. No.: WO2019/209185
PCT Pub. Date: Oct. 31, 2019

(65) Prior Publication Data
US 2021/0076963 A1    Mar. 18, 2021

(30) Foreign Application Priority Data

Apr. 27, 2018   (SG) ......................... 10201803570Q (51) Int. Cl.
| | |
|---|---|
| *A61B 5/316* | (2021.01) |
| *A61B 5/00* | (2006.01) |
| *A61B 5/369* | (2021.01) |
| *G06N 3/08* | (2023.01) |
| *G06N 20/10* | (2019.01) |
| *G08C 17/02* | (2006.01) |
| *G16H 20/30* | (2018.01) |
| *G16H 20/40* | (2018.01) |
| *A61F 4/00* | (2006.01) |

(52) U.S. Cl.
CPC ............ *A61B 5/316* (2021.01); *A61B 5/0006* (2013.01); *A61B 5/369* (2021.01); *G06N 3/08* (2013.01);
(Continued)

(58) Field of Classification Search
CPC ....... A61B 5/316; A61B 5/0006; A61B 5/369; G16H 20/30; G16H 20/40; G06N 3/08;
(Continued)

(56) References Cited

U.S. PATENT DOCUMENTS

| | | | |
|---|---|---|---|
| 8,463,371 B2 * | 6/2013 | Guan ..................... | A61B 5/374 600/545 |
| 10,013,777 B2 * | 7/2018 | Mariampillai ......... | A61B 6/505 |

(Continued)

FOREIGN PATENT DOCUMENTS

CN    102645589 A    8/2012

OTHER PUBLICATIONS

Lenhardt et al. "An Adaptive P300 Based Online Brain-Computer Interface", Apr. 2008, IEEE Publication, vol. 16, No. 2, pp. 121-130 (Year: 2008).*

(Continued)

*Primary Examiner* — Elias Desta
(74) *Attorney, Agent, or Firm* — Barnes & Thornburg LLP (57) ABSTRACT

Disclosed is a signal processing system for a brain machine interface (BMI) and a method performed by such a signal processing system. The method involves receiving and filtering input data comprising cortical signal samples, calculating a threshold for detection of spikes, identifying spikes in subsequently received samples, and outputting spike data corresponding to the identified spike or spikes.

20 Claims, 5 Drawing Sheets

(52) U.S. Cl.
CPC ............. *G06N 20/10* (2019.01); *G08C 17/02* (2013.01); *G16H 20/30* (2018.01); *G16H 20/40* (2018.01); *A61F 4/00* (2013.01); *G08C 2201/30* (2013.01)

(58) Field of Classification Search
CPC .... G06N 20/10; G08C 17/02; G08C 2201/30; A61F 4/00
See application file for complete search history.

(56) References Cited

U.S. PATENT DOCUMENTS

| | | |
|---|---|---|
| 2014/0073975 A1 | 3/2014 | Engelbrecht et al. |
| 2015/0088026 A1 | 3/2015 | Averina et al. |
| 2017/0065199 A1 | 3/2017 | Meisel |
| 2018/0000440 A1 | 1/2018 | Nishikawa |

OTHER PUBLICATIONS

Christie B. P. et al., "Comparison of spike sorting and thresholding of voltage waveforms for intracortical brain-machine interface performance", Journal of Neural Engineering, Dec. 11, 2014, vol. 12, No. 1, pp. 1-20.

Rey H. G. et al., "Past, present and future of spike sorting techniques", Brain Research Bulletin, Oct. 31, 2015, vol. 119, No. B, pp. 1-30.

Widmann A. et al., "Digital filter design for electrophysiological data—a practical approach", Journal of Neuroscience Methods, Jul. 30, 2015, vol. 250, pp. 1-16.

PCT Search Report and Written Opinion for PCT/SG2019/050236 dated Jul. 10, 2019.

* cited by examiner

SIGNAL PROCESSING SYSTEM FOR BRAIN MACHINE INTERFACE AND METHOD PERFORMED BY THE SYSTEM

CROSS REFERENCE TO RELATED APPLICATIONS

This application is a U.S. national stage application under 35 U.S.C. § 371(b) of International Application No. PCT/SG2019/050236 filed Apr. 29, 2019, which claims priority to Singapore Patent Application No. 10201803570Q filed on Apr. 27, 2018, the disclosures of both of which are hereby expressly incorporated by reference in their entirety.

TECHNICAL FIELD

The present invention relates to a method and system for robust signal processing in brain-machine interface (BMI) on an embedded digital signal processing (DSP) platform. More particularly, the present invention relates to a DSP system and a method for DSP on such a system.

BACKGROUND

Decoding neural cortical activity signals for the control of cursors, robotic arms and other assistive devices have been widely studied. This is a promising way for people with spinal cord injuries (SCI) or amyotrophic lateral sclerosis (ALS) to regain one or both of motor functions and the ability to communicate. Communication with the external world is especially important in improving the quality of life for those ALS patients who are in "locked in" state without any other means of communication.

The main limitation of current BMI systems that has prevented them from commercialization and widespread adoption is that most still use a wired connection from the subject to bulky and expensive machines for data acquisition, processing and decoding. Tethering a subject with wires from one or more electrode arrays to the signal processing unit largely limits its application and is undesirable cosmetically. Therefore, a wireless transmission system is needed for the practical usage of a BMI system.

There are two approaches for wireless transmission of neural data-high data rate (20-40 kHz) transmission of wide-band neural data, and low data rate transmission of only selected neural features for decoding. The advantages of the second method include lower power usage, a longer transmission range, smaller receiving antenna, cheaper implementation (e.g. bluetooth), and lower rates of dropped data.

In order to achieve the more robust low data-rate transmission, on-chip signal processing is crucial for extracting useful features from wide-band neural signals before wireless transmission. One of the features that is commonly used for decoding is the spike data, or single neuron action potentials. Several approaches exist in the literature that target robust spike detection for digital signal processor (DSP) on-chip implementation. Most of these methods require a pre-alignment of the waveforms to detect spikes, need a pre-calculated threshold or pre-obtained parameters for online spike detection. The methods are thus slow and require considerable power to generate an output.

In existing systems, threshold calculation typically occurs by sending a large amount of data from the DSP on-chip to a remote system, the remote system then processing that data, at a higher rate than an on-chip implementation may achieve, to determine the threshold. The threshold is then sent back to the chip for detection of spikes. To achieve this in real-time, or sufficiently rapidly to identify control commands with a useful response time, requires the chip to send a large amount of data in a very short period of time (e.g. 1 or 2 seconds), to the remote system. This uses a lot of energy. The alternative would be to implement the threshold determination on the chip, using the large amount of data, but this would use potentially more energy and also heat up the chip. Heating the chip can cause detriment to tissue surrounding the chip, particularly if the intention is ultimately to have a fully-embedded, implanted chip for spike detection and decoding.

It is generally desirable to overcome or ameliorate one or more of the above described difficulties, or to at least provide a useful alternative.

SUMMARY

It is desirable to enable low-bandwidth wireless transmission (LBWT) of the neural spike data from the brain cortex to a computer for efficient real-time decoding/classification in brain-machine interface (BMI). This will allow the user to be free from a tethered connection to a machine, which becomes especially important for applications related to mobility, and will allow the patients to regain the mobility. Few approaches are available in the prior art that target for efficient low-bandwidth, wireless transmission of spike features for digital signal processor (DSP) system (e.g. on-chip) implementation. Low-bandwidth transmission is important for robust wireless transmission, as well as to decrease power consumption. Most existing methods for such signal processing need offline training to obtain threshold or parameters.

Described herein is a system and methods, executed by that system, based on fixed-point computation for BMI neural spike decoding. The methods collectively perform the steps of 1) calculating the threshold based on recursive value-count tracking and adaptive threshold calculation for fixed-point implementation; 2) detecting the spikes by proposed crossing-transition triggered computation-efficient method, and 3) filtering the signal by precision-preserving fixed-point filter with overflow and underflow handling capability. Finally the spike information for each defined time interval is transmitted through a wired or wireless connection to a computer to be integrated with an online classification or continuous decoding engine to control the assistive devices.

Methods described herein for low-bandwidth transmission of the spike features may address the major hurdles in current BMI systems involving wired or high-bandwidth wireless transmission (HBWT) that largely limits the applications and usability of the BMI system.

As used herein, a brain-machine interface (BMI), sometimes referred to as a neural control interface, mind-machine interface, direct neural interface or brain-computer interface, is a communication pathway between a brain and an external device. A BMI may allow for bidirectional information flow. BMIs receive brain signals and can seek to extract information from those signals to, among other uses, assist in research, mapping (e.g. brain signals to intention), and augmenting or repairing human cognitive or sensory-motor functions.

Disclosed is a signal processing method on a signal processing system in a brain machine interface, comprising the processing steps of:

receiving input data comprising cortical signal samples;
applying a filter to the input data to obtain filtered data samples;
calculating a threshold by:
  initializing one or more parameters;
  recursively updating the one or more parameters based on a value of each filtered data sample;
  grouping each filtered data sample into an ordered set of groups, based on the value of the respective filtered data sample and the recursively updated one or more parameters;
  identifying a threshold group based on a number of filtered data samples grouped into groups distributed, around the threshold group, in the ordered set of groups; and
  determining the threshold based on the threshold group and the one or more parameters;
identifying a spike in each of one or more subsequently received data samples based on the threshold; and
outputting spike data corresponding to the spike or spikes identified in the one or more subsequently received data samples.

The term "signal processing system" may refer to a patient-mounted system—e.g. a device mounted or attached to the head of a subject, or other system that is with the patient—or a suitable mobile system. The signal processing system may be implemented on a chip (i.e. an on-chip implementation).

The signal processing system may communicate (in a wired or wireless fashion) with a remote system for spike decoding, or the signal processing system may itself perform spike decoding. The system may comprise an analogue-to-digital (AD) converter and/or signal multiplexer that takes a plurality of digital signals from the AD converter and multiplexes them, or one or both of the AD converter and signal multiplexer may be provided on an implantable multi-channel array.

The "groups" may be interchangeably referred to herein as "bins".

The input data may be measured by a sensor in a cortex of a patient. The sensor may be an implanted sensor. The sensor may be a multi-channel sensor (e.g. microelectrode) array. The sensor may thus be an implanted multi-channel sensor array, the signal processing system being connected, in some embodiments, to the implanted multi-channel sensor array and the processing steps being performed on cortical signal samples captured on each respective channel of the multi-channel sensor array. In other embodiments, the input data is received from a database or memory, or otherwise from a repository or store of cortical signals of a patient.

Initializing the one or more parameters may comprise setting:
  a maximum value (iMax);
  a minimum value (iMin); and
  a number of groups for the ordered set of groups.

Recursively updating the one or more parameters based on a value of each filtered data sample may comprise setting at least one of iMax and iMin to be, respectively, a maximum value and a minimum value across all of the filtered data samples. The method may further comprise calculating a dynamic range of the filtered data samples (iRng) based on the formula:

$$iRng = iMax - iMin + 1$$

Thus, the corresponding features may be corresponding parameters or characteristics, represented in the filtered data samples, that are the same as the one or more parameters though having potentially different values.

Grouping each filtered data sample into an ordered set of groups may comprise identifying, for each filtered data sample, a respective group of the ordered set of groups by normalizing each filtered data sample over iRng. Grouping each filtered data sample into an ordered set of groups may comprise identifying, for each filtered data sample, a respective group of the ordered set of groups may comprise normalizing each filtered data sample over iRng according to the formula:

$$iB = \frac{x(k) - iMin}{iRng} \times nBin$$

wherein iB is the bin index for the respective group, x(k) is a filtered data sample comprising k seconds of the input data, and nBin is the number of groups in the ordered set of groups.

Applying a filter to the input data to obtain filtered data samples may comprise applying a Finite Impulse Response (FIR) filter or an Infinite Impulse Response (IIR) filter to the input data. Applying a filter to the input data to obtain filtered data samples may comprise applying an IIR filter, and wherein the input data may have a first precision in which the cortical signal samples are each represented by a first number of bits, and applying an IIR filter to the input data may comprise applying a modified Direct Form I filter of order N, having 2N delay units, by:
  scaling upscaling filter coefficients b and scaling downscaling filter coefficients a to obtain scaled filter coefficients $\tilde{b}$ and $\tilde{a}$ respectively;
  casting an input signal x(n) and the scaled filter coefficients into a second precision, wherein x(n) comprises the input data and the second precision is higher than the first precision;
  applying the IIR filter to the input signal x(n), using $\tilde{b}$ and $\tilde{a}$ as coefficients for the IIR filter, to obtain an intermediate result; and
  downscaling the intermediate result into the first precision.

Scaling upscaling filter coefficients b and scaling downscaling filter coefficients a to obtain scaled filter coefficients $\tilde{b}$ and $\tilde{a}$ may comprise:
  applying the IIR filter to a stored set of cortical signal samples to produce a first set of filtered samples;
  applying a floating-point filter to the stored set of cortical signal samples to produce a second set of filtered samples;
  determining a number of precision bits $n_p$ resulting in a minimal difference between the first set of filtered samples and the second set of filtered samples, and scaling to $2^{n_p}$ to obtain the scaled filter coefficients $\tilde{b}$ and $\tilde{a}$.

As used herein, the term "difference" includes within its scope "errors", such as the "mean absolute error", the "mean square error", and so forth.

The intermediate result may have a first form y(n) and a second form, and applying the IIR filter to the input signal x(n), using $\tilde{b}$ and $\tilde{a}$ as coefficients for the IIR filter, may obtain y(n). In this case, the method may further comprise:
  obtaining the second form of the intermediate result by retaining a sign of y(n), casting y(n) to an unsigned integer format, wherein downscaling the intermediate result into the first precision comprises downscaling the second form of the intermediate result into the first precision.

The second form may be called $SY_f$, which may be obtained from y(n) by:
retaining the sign S of y(n);
casting y(n) to an unsigned integer format $Y_f$; and
bit-shifting $Y_f$ to obtain $SY_f$.

Bit-shifting $Y_f$ may comprise left shifting $Y_f$ to scale by $2^{n_r-n_p}$, wherein $n_r$ is a total number of bits used to represent x(n).

Also disclosed herein is a signal processing system for a brain machine interface, the signal processing system comprising:
a receiver for receiving cortical signals measured by a multi-channel sensor array;
a wireless transmitter for transmitting an output;
memory; and
at least one processor, the memory storing instructions that, when executed by the at least one processor, cause the at least one processor to, for each channel of the multi-channel sensor array:
receive input data at the receiver, the input data comprising cortical signal samples;
apply a filter to the input data to obtain filtered data samples;
calculate a threshold by:
initializing one or more parameters;
recursively updating the one or more parameters based on a value of each filtered data sample;
grouping each filtered data sample into an ordered set of groups, based on the value of the respective filtered data sample and the recursively updated one or more parameters;
identifying a threshold group based on a number of filtered data samples grouped into groups distributed, around the threshold group, in the ordered set of groups; and
determining the threshold based on the threshold group and the one or more parameters; and
identify a spike in each of one or more subsequently received data samples, received at the receiver, based on the threshold;
the instructions, when executed by the at least one processor, further causing the at least one processor to output the output, from the wireless transmitter to a remote system, the output comprising spike data corresponding to the spike or spikes identified in the one or more subsequently received data samples.

The input data and/or subsequently received data samples may be received at the receiver from (e.g. directly from) the multi-channel sensor array. Alternatively, the input data and/or subsequently received data samples may be received or extracted from a database or memory.

The at least one processor may be caused to apply a filter to the input data to obtain filtered data samples applying a Finite Impulse Response (FIR) filter or an Infinite Impulse Response (IIR) filter to the input data. Applying a filter to the input data to obtain filtered data samples may comprise applying an IIR filter, and the input data may have a first precision in which the cortical signal samples are each represented by a first number of bits, and the at least one processor may be caused to apply an IIR filter to the input data by applying a modified Direct Form I filter of order N, having 2N delay units, by:
scaling upscaling filter coefficients b and scaling downscaling filter coefficients a to obtain scaled filter coefficients b and a respectively;
casting an input signal x(n) and the scaled filter coefficients into a second precision, wherein x(n) comprises the input data and the second precision is higher than the first precision;
applying the IIR filter to the input signal x(n), using b and a as coefficients for the IIR filter, to obtain an intermediate result; and
downscaling the intermediate result into the first precision.

The at least one processor may be caused to scale upscaling filter coefficients b and scale downscaling filter coefficients a to obtain scaled filter coefficients $\tilde{b}$ and $\tilde{a}$ by:
applying the IIR filter to a stored set of cortical signal samples to produce a first set of filtered samples;
applying a floating-point filter to the stored set of cortical signal samples to produce a second set of filtered samples;
determining a number of precision bits $n_p$ resulting in a minimal difference between the first set of filtered samples and the second set of filtered samples, and
scaling to $2^{n_p}$ to obtain the scaled filter coefficients $\tilde{b}$ and $\tilde{a}$.

The "difference" between the first set of filtered samples and the second set of filtered samples may be referred to herein as an "error" or "errors".

The intermediate result may have a first form y(n) and a second form, and the at least one processor may be caused to:
apply the IIR filter to the input signal x(n), using $\tilde{b}$ and $\tilde{a}$ as coefficients for the IIR filter, to obtain y(n); and
obtain the second form of the intermediate result by retaining a sign of y(n), casting y(n) to an unsigned integer format,
wherein downscaling the intermediate result into the first precision comprises downscaling the second form of the intermediate result into the first precision.

The second form may be called $SY_f$, and the at least one processor may obtain $SY_f$ from y(n) by:
retaining the sign S of y(n);
casting y(n) to an unsigned integer format $Y_f$; and
bit-shifting $Y_f$ to obtain $SY_f$.

The at least one processor may be caused to bit-shift $Y_f$ by left shifting $Y_f$ to scale by $2^{n_r-n_p}$, wherein $n_r$ is a total number of bits used to represent x(n).

The at least one processor may further be caused to perform the steps of the method described above, in any applicable combination.

Also disclosed is a brain machine interface comprising a signal processing system as described above. The signal processing system may implement a method as also described above.

Also disclosed is a system (comprising or being a signal processing system as described above, which may run the methods also described above) for efficient and robust implementation of, for example, on-chip signal processing algorithms such as filtering, threshold calculation and spike detection for neural spike signals. Embodiments of the proposed system comprise a recursive value-count tracking-based adaptive threshold calculation for fixed-point implementation, a crossing-transition triggered computation-efficient spike detection method and a precision-preserving fixed-point filter method with overflow and underflow handling capability. Advantageously, experimental evaluation of the methods disclosed herein showed no significant degradation in performance compared to the floating-point method.

A system is disclosed, implementing robust signal processing for a neural spike signal to facilitate the system-on-chip implementation in BMI—the skilled person will appreciate the signal processing system may be implemented in ways other than using a system-on-chip implementation. The system may employ one or more of:
(a) recursive value-count thresholding.
(b) crossing-transition triggered spike detection.
(c) precision-preserving fixed-point filter.

The recursive value-count thresholding may be recursive value-count tracking-based thresholding. That thresholding process may be adaptive—e.g. adaptive to changes or variations in EEG data. That thresholding process may be used for fixed-point implementation, such that it is recursive value-count tracking-based adaptive thresholding for fixed-point implementation (RVCT-aTrFx).

The cross-transition triggered spike detection may be crossing-transition triggered computationally efficient spike detection (CTT-SPD).

The precision-preserving fixed-point filter may employ or provide overflow/underflow handling (PPFF-FwHd).

The proposed adaptive thresholding (RVCT-aTrFx) may perform one or more of:
(a) Recursively tracking the dynamic ranges of samples to establish an efficient representation.
(b) Computing the basic threshold based on the distributions of samples in the value-count profile.
(c) Calculating the threshold adaptively at a predefined time interval with efficient buffer management.

The proposed crossing-transition triggered spike detection (CTT-SPD) may:
(a) detect spikes only when a crossing-transition exists in the processing sample and its previous immediate neighboring sample (PV-INS) (reduce computational complexity)
(b) identify the entering point of the edge of a spike or spikes with defined local fluctuation measure.

The proposed filtering (PPFF-FwHd) may employ:
(a) IIR band-pass filter-low in delay and computational complexity. Select proper low cut-off frequency to remove line noise and local field potential.
(b) Choose the precision bit to convert filter coefficients by minimizing the difference of the filtered data obtained from fixed-point and floating-point filter.
(c) Preserve data precision by "double-scaling": firstly scale up to a higher precision and protect the sign. Then scale down to original data precision after filtering.
(d) Automatically handle underflow/overflow by preserved bits.

The signal processing system in BMI may thus perform:
(a) adaptive thresholding (RVCT-aTrFx) by:
 (i) recursively tracking the dynamic ranges of samples so that an efficient value-count based representation can be established;
 (ii) computing basic threshold based on sample distributions of value-count profile; and
 (iii) adaptively computing the threshold by dynamically refreshing the buffer;
(b) crossing-transition triggered spike detection (CTT-SPD) by:
 (i) performing spike detection only when a crossing-transition is detected (reduce computational load); and
 (ii) setting one or more effective local conditions to detect the spike for each crossing;
(c) precision-preserving filtering (PPFF-FwHd) by:
 (i) choosing the precision bit used to convert filter coefficients by minimizing the difference between filtered data obtained from the fixed-point filter and that from the floating-point filter; and
 (ii) solving underflow/overflow by preserved bits, and preserving data precision by double-scaling.

Advantageously, the methods and signal processing system for digital signal processing (DSP), particularly for DSP chip implementation, disclosed herein may:
(a) facilitate low-bandwidth wireless transmission of neural spike features from brain cortex to a computer for online decoding;
(b) allow users to be free from a tethered connection to a machine, which becomes especially important for applications related to mobility and allows users to regain mobility.

BRIEF DESCRIPTION OF THE DRAWINGS

Preferred embodiments of the invention are hereafter described, by way of non-limiting example only, with reference to the accompanying drawings, in which.

DETAILED DESCRIPTION OF PREFERRED EMBODIMENTS

The following detailed description sets out embodiments of a signal processing system (which may be mounted or attached to a scalp of the subject (e.g. a patient) and connect with a multi-channel (e.g. microelectrode) array implanted in the motor cortex of the subject, or the signal processing system may itself be implantable—e.g. with the microelectrode array), system (which may be, or comprise, the signal processing system) and methods executed by the signal processing system that employ a fixed-point implementation to compute neural spike features from cortical signals to facilitate DSP implementation in a brain machine interface (BMI).

The purpose of some embodiments is to enable the low-bandwidth, wireless transmission of the spike firing rate for BMI decoding. This can allow the user to regain free-range movements with the removal of the wired connection between the brain and the processing computer. Unlike existing approaches that require offline training to obtain a threshold or other parameters for online processing, the methods proposed herein compute the threshold by dynamic value-count tracking, which allows for adaptive thresholding by iteratively updating a buffer as described below. The threshold computation is based on recursive value-count tracking that approximates the median-based threshold with proven robustness and non-sensitivity to noise. The final spike detection is triggered by the crossing-transitions to reduce the computational power. This method possesses the lowest, or very low, computational load making it suitable for a signal processing system in, for example, an on-chip implementation.

In order to transmit the neural spike signals from the brain cortex to a computer wirelessly, fixed-point DSP has been found to be easy to integrate with applications. However, the overflow and underflow, and round-off noise has to be considered for each operation of fixed-point implementation. Most existing methods for signal processing systems, particularly those that are mounted to the patient or are otherwise on-chip implementations, require an offline training process to obtain the threshold for online processing. As taught herein, novel methods are proposed for performing fully online signal processing and wireless transmission of the neural spike data. In particular, proposed is a recursive value-count tracking-based method to calculate the threshold adaptively, an efficient spike detection method triggered by crossing-transition, and a precision-preserving fixed-point filter that is able to handle the overflow/underflow automatically with the preserved bits.

Figure 1:
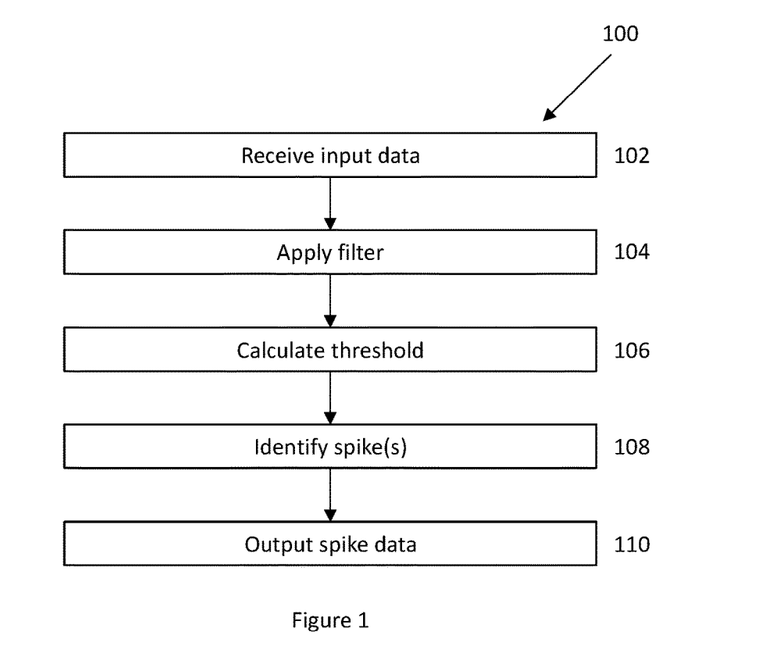
FIG. 1 is a schematic diagram of a method for DSP on a signal processing system, with the steps of the method being performed in an exemplary order.

FIG. 1 is a schematic diagram of a signal processing method 100 for a signal processing system in a BMI. The method 100 broadly comprises the processing steps of:

102: receiving input data comprising cortical signal samples;

104: applying a filter to the input data to obtain filtered data samples;

106: calculating a threshold;

108: identifying a spike in each of one or more subsequently received data samples based on the threshold; and 110: outputting spike data corresponding to the spike or spikes identified in the one or more subsequently received data samples.

Figure 2:
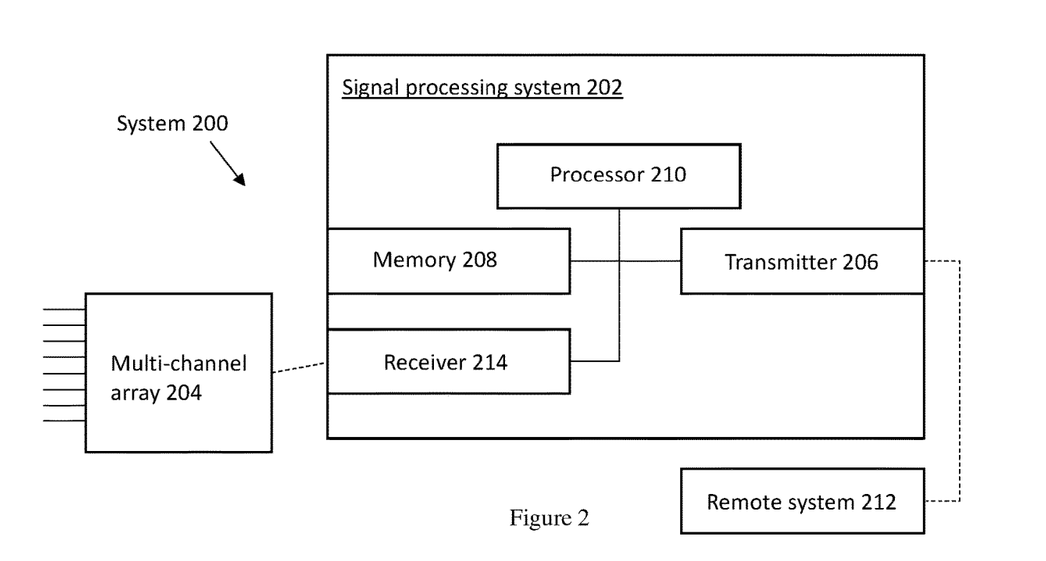
FIG. 2 is an embodiment of a system for performing the method of FIG. 1.

The method 100 may be performed on a system 200, as shown in FIG. 2, including a signal processing system 202 (which may be a chip), e.g. for DSP. The signal processing system 202 comprises a transmitter 206 for transmitting an output, memory 208, at least one processor (for ease, hereinafter the processor 210) and a receiver 214 connectable to a multi-channel array 204 for sensing cortical signals. The memory 208 stores instructions that, when executed by the processor 210, cause the processor 210 to perform the method using the array 204, transmitter 206 and memory 208, receiver 214 for each channel of the multi-channel array 204. The memory 208, or a different memory or database, may also store cortical signals. The processing steps of method 100 are performed on cortical signal samples captured on each respective channel of the multi-channel array 204. The signal processing system 202 may incorporate the array 204 but, in the present embodiment, is connected to the array 204 via a hardwired connection or a wireless connection as indicated by the broken lines.

As will be appreciated by the skilled person, wired or wireless transmission may be achieved using any suitable method and protocol. As mentioned above, the connection between system 212 and array 204 may be hardwired—e.g. by a wire passing through the scalp to the array 204 implanted in the cortex of the subject, or where the system 202 and array 204 form part of the same device they may both be implanted on the cortex together to facilitate communication of measured cortical signals—or by wireless connection—e.g. by providing an antenna, or micro antenna, on the array 204 and an antenna of the system 202, the antenna or micro antenna on the array potentially only being part of a transmitter rather than a transceiver. The system 202 may similarly communicate with the remote system 212 wirelessly, using the same or different antenna to that used to communicate wirelessly with the array 204, or in a hardwired configuration—the latter is less preferable since it requires the subject to be near the remote system 212 during signal decoding. The skilled person will understand such arrangements and variations thereon, all of which are intended to form part of the present disclosure.

The system 200 of the embodiment shown in FIG. 2 also includes a spike decoding system (i.e. remote system 212), in wired or wireless communication with the transmitter 206 (thus making the transmitter a wired or wireless transmitter, respectively), for receiving spike data from the transmitter 206 and decoding the spike data to determine control commands.

Many of the methods provided in accordance with method 100, for implementation by system 200, in BMI decoding are described below and consist of methods for recursive value-count tracking-based adaptive threshold calculation for fixed-point implementation (RVCT-aTrFx), crossing-transition triggered spike detection (CTT-SPD) and precision-preserving fixed-point filter with automatic overflow/underflow handling (PPFF-FwHd). The objective as described above is to facilitate the low-bandwidth wireless transmission of the neural spike features from the brain cortex to a computer for online decoding to control an assistive device. Such implementation is important to allow the users to be untethered. As a result, the subjects can be relieved from restricted movements, infection, and other noise and electrical interference.

Figure 3:
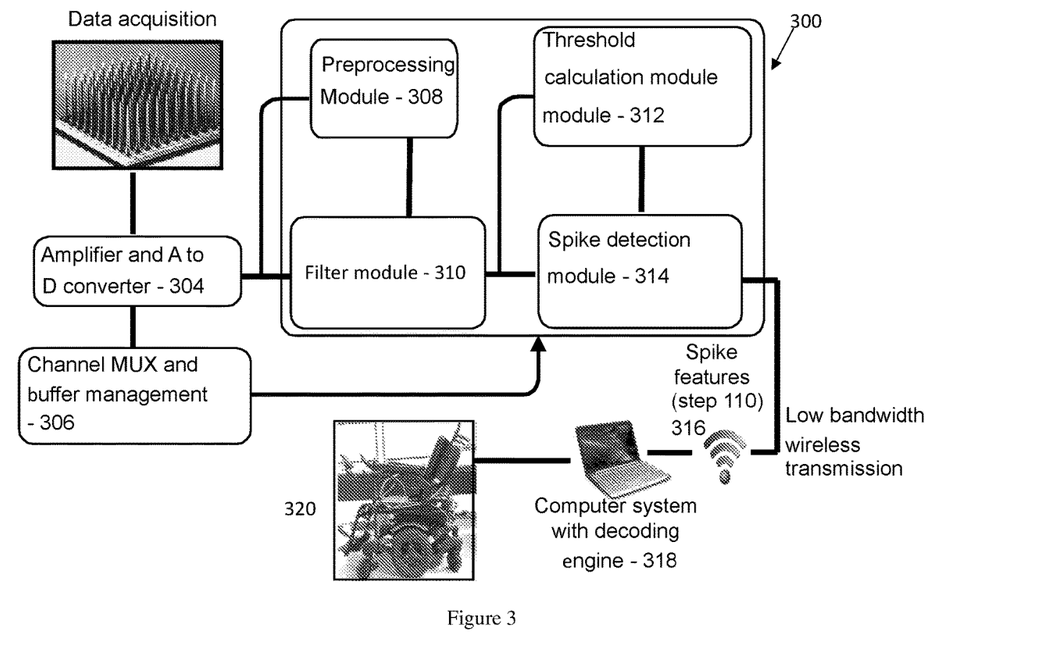
FIG. 3 is a schematic block diagram of an embodiment of an overall system integrating a signal processing engine for signal processing system in accordance with present embodiments with the decoding/classification engine.
Figure 6:
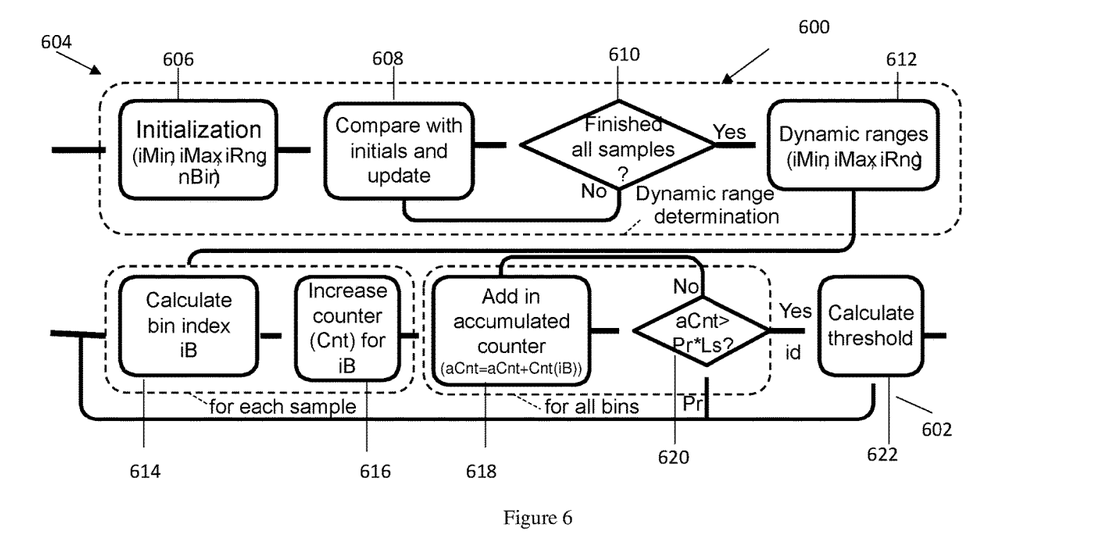
FIG. 6 is a block diagram illustrating a threshold calculation method in accordance with method 100, specifically a RVCT-aTrFx method.

The system 200 employs a method for calculating the threshold by dynamically tracking value-count—see block 312 of FIG. 3 and FIG. 6—of the cortical signal samples for the purpose of detecting spikes in BMI for the fixed-point implementation.

As will be described in more detail, the important features in threshold calculation method are:

1) Recursively tracking of the dynamic ranges of samples so that an efficient value-count based representation can be established. The bin or group number is selected to store the samples based on the dynamic ranges and maximum values of the samples.

2) Computing the basic threshold (i.e., estimation of the standard deviation of background noise) based on the distributions of the samples in the value-count profile.

3) Calculating the threshold adaptively at a predefined time interval with buffer management. In some instances, adaptive calculation may not be required.

As described with reference to block 312 of FIG. 3 and the exemplary embodiment in FIG. 6, the above steps were achieved by:

a) Dynamically tracking the samples to find the ranges of the values of the samples by iteratively updating the minimum and maximum, till all the samples were processed (e.g. taking each sample as a single data point and identifying a maximum and minimum value of the data points for a given set of samples).

b) Recursively tracking the value-count by throwing the samples into the proper group or bin based on the value of the given sample. The number of samples contained in each bin were dynamically added to the accumulated counter, until the counter value was larger than the defined distribution criterion—e.g. the median (e.g., 50% of total number of samples)—and the relevant bin (or its bin index) was selected.
c) Taking the corresponding value of the selected bin index as the basic threshold.
d) Scaling the basic threshold based on the parameters given which can be obtained from offline or asynchronous training based on history data to optimize the classification accuracy.
e) Calculating the threshold based on the latest k seconds of data in the buffer which was refreshed for every n seconds, where k and n were determined based on the buffer condition and processing speed requirements.

The system 200 also employs a method for detecting spikes, detection being triggered by crossing-transition as described with reference to block 314 of FIG. 3, and FIG. 7. As will be described in more detail below, the important features for this method are:

1) Defining a trigger criterion to detect the spikes only when a crossing-transition exists in the processing sample and its previous immediate neighbouring sample (PV-INS). This significantly reduces the computational complexity since the crossings only occupy a small portion of the original samples.
2) Defining a local fluctuation measure to identify the entering point of the edge of spikes.

In one exemplary embodiment, this process involved:
a) Identifying a crossing when the sum of the sample (i.e. sample value) and the threshold was less than zero.
b) Examining its PV-INS when a crossing transition was detected (i.e., only one of the sample and its PV-INS was a crossing). If the value of PV-INS was larger than the processing sample, an entering point of the edge of a spike was detected, hence a spike was detected.

Figure 4:
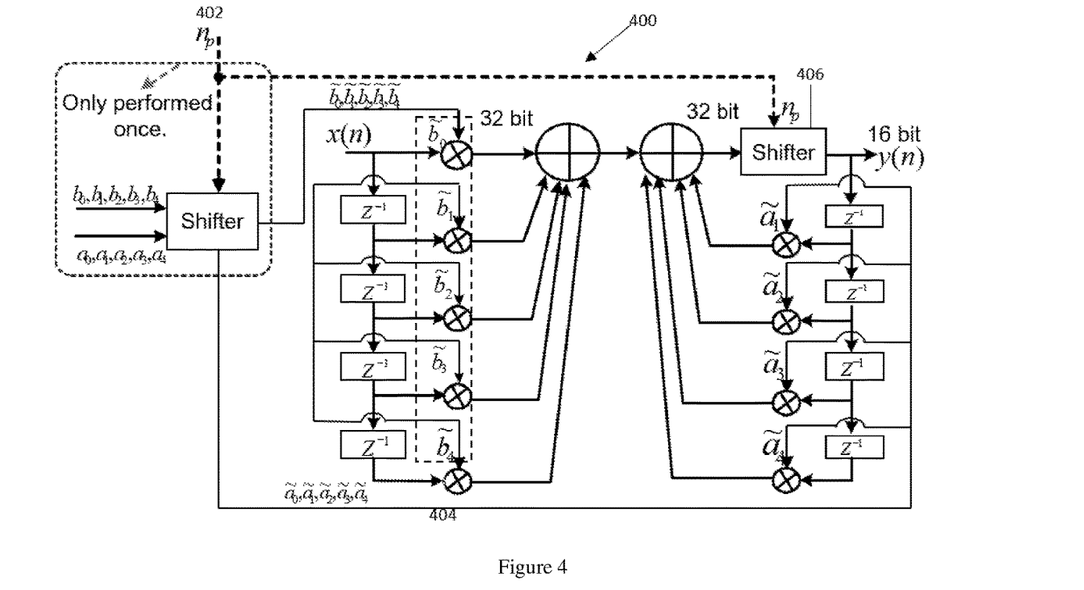
FIG. 4 illustrates a "precision-preserving fixed-point filter with overflow/underflow handling (PPFF-FwHd)" in accordance with method 100.
Figure 5:
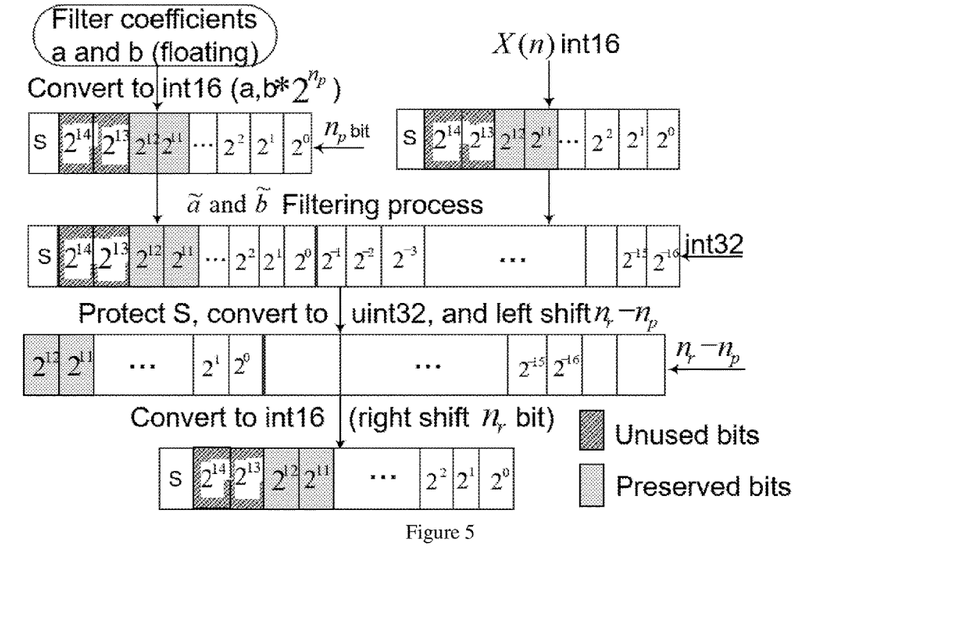
FIG. 5 is an illustration of the bit-shifting process performed during filtering according to FIG. 4.

The system 200 also employs a method for filtering the raw cortical signal based on fixed-point computation to facilitate DSP implementation—see block 310 of FIG. 3, and FIGS. 4 and 5. The important features of this filtering process are:

1) Choosing the precision bit used to convert the filter coefficients and represent the input data ($n_p$) by minimizing the difference between the filtered data obtained from fixed-point filter and that from floating-point filter.
2) Preserving the data precision by "double-scaling" technique. The data samples (through multiplying by the filter coefficients) were firstly scaled up to a higher precision and the signs were protected. After filtering, the intermediate results were scaled down to the original data precision for processing the next sample.
3) Automatically handling the underflow and overflow using the preserved bits, i.e., the difference between the determined precision bit ($n_p$), and the actual bits representing the input data ($n_a$), generally $n_p > n_a$.

Importantly, the proposed system and method can be integrated with any decoding/classification method by transmitting the computed spike features (spike data) wirelessly to a computer where the engine of decoding/classification and control of prosthetic device resides. Such low-bandwidth features will allow efficient decoding the neural spiking signal in real time to control an assistive device.

The purpose of the system 200 and method 100 is to enable the low-bandwidth, wireless transmission of the spike firing rate for BMI decoding. This will allow the user to regain free-range movements with the removal of the wired connection between the brain and the processing computer. Unlike most existing approaches that require offline training to obtain a threshold or other parameters for online processing, our proposed method computed the threshold by dynamically value-count tracking, which allows for adaptive thresholding by iteratively updating the buffer. The threshold computation was based on recursive value-count tracking (tracking the number of samples with each respective value from a set of all possible values) which approximated the median-based threshold with proved robustness and non-sensitiveness to noise. The final spike detection was triggered by the crossing-transitions to reduce the computational power. This method possessed the lowest computational load making it suitable for on-chip implementation.

Overall System

An example overall system 300 integrating the present method 100 of signal processing for, for example, DSP chip implementation with the decoding/classification engine, to control mobile robots such as controlling a wheelchair is shown in FIG. 3. The system 300 is represented as functional blocks that can be implemented by the memory 208 (e.g. incorporating a buffer), transmitter 206, array 204 and processor 210. The decoding can ultimately be performed by remote system 212, corresponding to computer 318.

FIG. 3 illustrates the proposed overall system integrating the presently proposed signal processing engine (e.g. for DSP chip implementation) with the decoding/classification engine stored in a remote computer 318—such as remote system 212.

The raw data (i.e. measurements) obtained from the multi-channel array 204, presently microwire electrode arrays 302 (i.e., data recording device) were amplified and the amplified raw data were then analog-to-digital converted at block 304, and subsequently multiplexed at block 306. Hence, proper de-multiplexing techniques were employed to obtain data channel by channel. The amplification and multiplexing blocks 304, 306 may be on the same chip or device as the multi-channel array 204, and/or may constitute components of signal processing system 202 (e.g. in the same housing as signal processing system 202).

The initial data (filtered data samples) for calculating the threshold (i.e., Dt-Tr) were extracted from the beginning of data (e.g., 0.5 second of data (referred to with reference to FIG. 6 as k seconds of data) by skipping the unstable part at the very beginning) and buffered in a buffer. Dt-Tr can be iteratively updated with more data (i.e. subsequently received cortical signal samples).

The buffer can be refreshed with new data after a predefined time interval, i.e., by the buffer management block. Hence, the threshold calculation can operate in adaptive mode.

Subsequent data were sequentially read to calculate firing rate (Dt-FR). Thus, while method 100 appears to propose a specific sequence of steps, those steps may be skipped or performed as needs be—e.g. the threshold need not be calculated for every set of input data.

The data was pre-processed at block 308 before the filtering process was executed at block 310 (corresponding to FIG. 4). Pre-processing may involve any appropriate data manipulation, such as centering the data to remove DC drift (i.e., the mean of the data was not centred at zero), which can be done by deducting the mean of data for the chosen time segment.

The pre-processed data outputted by block 308 were then cast to the format with the same precision as the input (denoted as $X_{cTr}$). $X_{cTr}$ were filtered with a precision-preserving fixed-point filter with overflow/underflow handling, discussed with reference to block 310 and FIG. 4, to obtain $X_{fTr}$. Thresholds were calculated based on a recursive value-count tracking-based adaptive threshold calculation method, discussed with reference to block 312 and FIG. 6, to obtain $T_r$.

The same procedure was carried out for subsequent data to calculate the firing rate, i.e., Dt-FR. The data were pre-processed the data to obtain $X_{cFr}$ and filtered the data to obtain $X_{fFr}$. The spikes were detected based on a crossing-transition triggered spike detection (CTT-SPD) method discussed with reference to block 314 and FIG. 3. A certain decoding bin width (e.g. 20 ms, 50 ms, 100 ms or otherwise as desired) was employed to refresh the counter timely, e.g., every 100 ms to output the firing rate (FR) for all the channels. Note that the processed samples can be adaptively buffered and used to calculate the mean (or other distribution characteristic as discussed with reference to FIG. 6) of the data.

The output FR can be wirelessly transmitted (316) to a computer (212, 318) where a decoding or classification engine resides. The final decoding results can then be used to control a mobile robot such as wheelchair (320) to allow the user to achieve mobility.

Embodiment of Step 104—Precision-Preserving Fixed-Point Filter with Overflow/Underflow Handling (PPFF-FwHd)

The main concept behind the present filter design for BMI is to keep the computational complexity low to facilitate signal processing system implementation, such as on-chip implementation, while preserving precision of data. An infinite impulse response (IIR) filter was chosen due to the fact it could meet given specifications with much lower order compared with that of finite impulse response (FIR) filters which may also be used in some implementations. This may significantly conserve the number of computations required per time step.

A disadvantage of IIR filters is the nonlinear phase. However, the non-linear phase may be eliminated by offline (or asynchronous) implementation with non-causal, zero-phase filtering.

The filter 400 proposed in FIG. 4 employs a modified Direct Form I (MDF-I) design, with 2N delay units for both input and output signals for a filter of order N. The filter 400 also comprises a "Shifter" engine that operates directly on the input filter coefficients and intermediate results.

The precision bits ($n_p$) were firstly determined offline (or asynchronously) based on historical data. The determination was made to minimize the errors or differences between the filtered data obtained from using a fixed-point filter and that of floating-point filter.

Typically $n_p < n_r$ (the unused bits $n_{ub} = n_r - n_p$), where $n_r$ is the total number of bits used to represent input data, e.g., 16 bits. However, the number of precision bits ($n_p$) is typically larger than that of the actual precision of input data ($n_a$), e.g., a first number of bit such as 10 bits. The preserved bits may therefore be denoted as $n_{pv} = n_p - n_a$. The preserved bits can be used to automatically handle the underflow and overflow problem, where the summation would otherwise result in a number outside the range capable of being specified by the number of precision bits.

A double-scaling process was then employed. The first scaling process is to scale the filter coefficients up to the precision bits (i.e., multiply by $2^{n_p}$). This will only be performed once before the filtering process. The second scaling process is firstly to scale the intermediate results up to the power of $2^{n_r - n_p}$ and scale down to the total number of bits used to represent the input data ($n_r$). Hence, overall the data are scaled down to $2^{n_p}$. This ensures that the input data and output filtered results are always of the same precision. Thus precision is "preserved".

The proposed method 400 has therefore been named "precision-preserving fixed-point filter with overflow/underflow handling (PPFF-FwHd)" for DSP implementation in BMI. This is illustrated in FIG. 4. In the present example, the filtering process was carried out in a higher precision buffer (e.g., int32) to avoid overflow as well.

Detailed Filtering Process

The PPFF-FwHd may perform the following steps:

Upscaling filter coefficients b and downscaling filter coefficients a were scaled to obtain scaled filter coefficients $\tilde{b}$ and $\tilde{a}$ respectively (402). The filter coefficients (a and b) were thus scaled to $2^{n_p}$ to obtain $\tilde{a}$ and $\tilde{b}$. $\tilde{a}$ and $\tilde{b}$ were then cast to the same precision as the input data, e.g., int16. In some embodiments, this step can be considered part of the filter 400, though it has been performed in advance of the steps represented schematically in FIG. 4—the proposed "precision-preserving fixed-point filter with overflow/underflow handling (PPFF-FwHd)".

The input signal x(n) and the scaled filter coefficients are cast into a second precision (note the precision of the input signal is specified above as being of a first precision), wherein x(n) comprises the input data received at step 102. Moreover, the second precision is higher than the first precision. In other words, the input signal (x(n)) and scaled filter coefficients ($\tilde{a}$ and $\tilde{b}$) were cast into a higher precision of integer format (e.g., "int32") to avoid overflow during computation.

A buffer (Y) is then initialised to store the intermediate results with size y=zeros(1,length($B_r$)) where $B_r$=[zeros(t,1); x(:)], t=max($L_b$, $L_a$−1), and $L_b$ and $L_a$ are where the length of filter coefficients a and b, respectively; x(:) represents all the input samples.

For each sample x(n), the filter (e.g. IIR filter) is applied using $\tilde{b}$ and $\tilde{a}$ as coefficients to obtain an intermediate result. The intermediate result may be obtained based on Equation (1):

$$y(n) = \tilde{b}_0 * x(n) + \tilde{b}_1 * x(n-1) + \ldots + \tilde{b}_{nb} * x(n-nb) - \tilde{a}_1 * y(n-1) - \ldots - \tilde{a}_{na} * y(n-na) \qquad (1)$$

where nb=$L_b$−1, na=$L_a$−1.

In the present embodiment, the intermediate result has a first form y(n), described above. The intermediate result also has a second form obtained by retaining the sign of y(n) and casting y(n) to an unsigned integer format. Thus, the sign S of y(n) is kept and y(n) is cast to an unsigned integer format, $Y_f$=cast(y(n)*s,'u int32'). In this case, y(n) is converted to positive when it is negative. It is the second form of the intermediate result that is subsequently downscaled into the first precision—e.g. the precision of the input data.

The second form may further involve bit-shifting $Y_f$—e.g. left-shifting to scale $Y_f$ by $2^{n_r - n_p}$-bit to obtain $sY_f$ (406).

The intermediate results $sY_f$ are then downscaled to the first precision—i.e. the same precision as the precision of the input data ($n^r$, e.g., "int16"). The most significant bits of y(n) are then kept for the calculation of next sample—this may be achieved by right shifting out the extra bits from the intermediate results (e.g. 32 bits) to downscale back to the input data precision (e.g. 16 bits), with the least significant bits thus being discarded.

These steps are reiterated until all the samples are processed.

An illustration of the bit shift during filtering process is shown in FIG. 5.

An exemplary embodiment of the IIR filter employed in accordance with FIGS. 4 and 5 is the Chebyshev Type II band-pass filter of order 2. The parameters of one example are set in Table I. Considering the fact that the spikes are high frequency fluctuations, these frequencies are selected to eliminate interference from low frequency and power line noise. The floating coefficients and its fixed-point counterparts (converted based on data precision of 14 bits, sampling rate of data is 12,987 Hz) are presented in Table II. The Chebyshev Type II filters have flat passbands with wide transition bands, in contrast to that of the Chebyshev Type I and elliptic filters with fast roll off and ripples in passband.

TABLE I

Parameter settings for Cheby2 band-pass filter

| Item | Parameter | Values |
| --- | --- | --- |
| 1 | Low stop | 80 Hz |
| 2 | Low cut-off | 300 Hz |
| 3 | High cut-off | 5000 Hz |
| 4 | High stop | 6000 Hz |
| 5 | Stopband ripple | 30 dB |
| 6 | Passband loss | 6 dB |

TABLE II

Coefficients for Cheby2 band-pass filter with the parameters defined in Table I.

| Filter type | Filter coefficients | Coefficients values |
| --- | --- | --- |
| floating | B | 0.485235041197720 −0.013531256974626 −0.941960738398651 −0.013531256974625 0.485235041197720 |
| | A | 1.000000000000000 −0.964164865350100 −0.355831162559359 0.108373032453001 0.257375778830363 |
| Fixed point | B | 7950 −222 −15433 −222 7950 |
| | A | 16384 −15797 −5830 1776 4217 |

Embodiment of Step 106—Recursive Value-Count Tracking-Based Adaptive Threshold Calculation for Fixed-Point Implementation (RVCT-aTrFx)

A recursive value-count tracking-based fixed-point thresholding (RVCT-aTrFx) method was designed to accommodate the narrow range of the filtered integer data (i.e. values of the filtered data samples). By recursively finding the dynamic range of the data, a fixed number of groups (i.e. bins) can be defined and used to store the value-count of filtered data (the number of filtered data samples having each value in the range of possible values).

A threshold can subsequently be calculated based on the defined criteria by considering distributions of the value-count profile. An exemplary embodiment of such criteria is the median, which is the "middle" value that separates the higher part from the lower part of the samples. The bin index for such a median value (e.g., $50^{th}$ percentile—i.e. there are up to 50% of samples with higher values, and up to 50% of samples with lower values) can be found and its sample value taken as the initial threshold.

The final threshold may then calculated by properly scaling the initial threshold to approximate the standard deviation (e.g. a single deviation, though multiple standard deviations may be used in some embodiments) of the background noise. This process is recursively applied to all data segments. An adaptive threshold mode is proposed below, where the threshold is calculated adaptively at a predefined time interval with proper buffer management. For example, the threshold can be calculated based on the latest k seconds of data which are refreshed every n seconds, where k and n can be determined based on the buffer condition and processing speed requirements.

A block diagram 600 illustrating an exemplary embodiment of the proposed RVCT-aTrFx method is shown in FIG. 6 with the detail steps described as follows, in accordance with method 100 of FIG. 1. The block diagram 600 comprises an upper part 602 and a lower part 604. The threshold calculation in the lower part 604 can be done for all the adaptively buffered time segments for each predefined time interval (e.g. k seconds) discussed above.

Firstly, filtered data is received per step 104, from the filtered described with reference to FIGS. 3 to 5. Diagram 600 then performs step 106 of method 100, namely calculation of a threshold or thresholds.

Block 606 involves initialisation of one or more parameters. This may involve setting initial values for a maximum value (iMax), a minimum value (iMin), and a number of groups (interchangeably referred to as "bins"), that may form an ordered set of groups of non-overlapping, ordered values or values ranges (e.g. spike values). A range of the data (iRng) may also be specified, or determined from iMax and iMin, or set to 0, when required. In the present embodiment, at block 606, the method 100 initializes the maximum (iMax), minimum (iMin) and range of the data (iRng) (e.g., −32768, 32767, 0 for input data of "int16"). The number of bins is also initialised based on available values—i.e. the available values for the filtered data (e.g., nBin=256). This may be determined based on historical data (from the subject in question or from a pool of subjects) or a first predetermined period of data. An accumulating counter aCnt may also be initialised (e.g. set to 0).

The absolute value for each sample may then be taken for subsequent processing.

At blocks 608, 610 and 612 the one or more parameters are updated based on values of the filtered data samples (i.e. a value of each respective filtered data sample). In the present embodiment, iMax and iMin are updated at block 608 by comparing each of them with the value (e.g. absolute values specified above) of the each sample, until all samples are processed—decision block 610. The dynamic range is obtained by the formula iRng=iMax−iMin+1 when all samples are processed—block 612—where iMin and iMax can be cast to the next lower or higher power of 2 for efficient implementation.

Thus iMax and iMin are set to be, respectively, a maximum value and a minimum value across all of the filtered data samples for the processed k seconds of data—i.e. all the adaptively buffered time segments for each predefined time interval.

Blocks 614 and 616 involve grouping the filtered data samples into bins—e.g. an ordered set of groups—based on a value in each filtered data sample and parameter(s) recursively updated at blocks 608, 610 and 612. Blocks 614 and 616 effectively perform recursive value-count tracking. This process throws all the values (e.g. filtered data samples) into proper bins by calculating the bin index for each sample (e.g., x(k)) by $$iB = \frac{x(k) - iMin}{iRng} \times nBin$$

in other words, for each filtered data sample, a respective bin is identified by normalizing the value of each filtered data sample over iRng.

Once the relevant bin has been identified—i.e. the bin associated with the relevant bin index—the counter for the relevant bin is incremented by Cnt(iB)=Cnt(iB)+1.

Blocks 618 and 620 use the bin counters from block 616 to identify a threshold bin based on a number of filtered data samples grouped into bins distributed around the threshold bin. Presently, the median is used—i.e. the threshold bin is the bin containing the median sample value—e.g. 50% of samples have either the same sample value of lower, and 50% of the samples have either the same sample value or higher where the 50% in each case can include the median sample. To achieve this, the count (Cnt) for all bins is added to the accumulating counter aCnt, i.e., aCnt=aCnt+Cnt(iB), until aCnt>Pr*Ls, where Ls denotes the total number of samples, and Pr denotes the chosen percentage to approximate the distribution (e.g., 0.5, or 50%, for median).

For the following calculations, we assume the bin index of the bin containing the median (or relevant value as determined by Pr) is "id".

Block 622 involves determining the threshold based on the threshold group or bin (id) and the one or more parameters.

The threshold is calculated by the formula $$Tr = C1 \times \left(\frac{id \times iRng}{nBin} + iMin\right) \Big/ C2,$$

where C1 and C2 are the constants used to scale the basic threshold obtained. C1 and C2 were obtained by optimizing the classification accuracy based on history data, normally C1>1&C1<10, C2<1 & C2>0.

The buffer containing the last k seconds of samples is then refreshed and blocks 606 to 622 re-executed until all of the samples are processed.

It is noted that the data used for detecting dynamic ranges (Dt-Dr) and calculation of the threshold (Dt-Tr) can be the same or different. The computational load can be saved if the dynamic range is determined once and applied for all subsequent data—e.g. buffered samples. However, this may compromise some precision in the determined threshold.

Embodiment of Step 108—Crossing-Transition Triggered Spike Detection (CTT-SPD)

The basic concept behind spike detection is finding a local valley in the sample data. In the present embodiment, to produce a computationally-efficient method, detection will only be triggered if a transition in threshold crossing is found, i.e., if the difference in values between one the processing sample and its previous immediate neighboring sample (PV-INS—the sample immediately before the current sample being processed) is a crossing (crosses the threshold calculated at step 106). The method is hence named "crossing-transition triggered spike detection (CTT-SPD)".

The crossings can be obtained once the threshold for each channel is obtained. In one embodiment, a minimum-sized window of two samples is considered to further expedite the processing speed. To identify whether or not a sample is a spike, the sample is compared with its PV-INS. The conditions for identifying a crossing are defined as (a) if a crossing-transition is detected and (b) the value of PV-INS is larger than that of the processing sample. The sample that satisfies conditions a) and b) is identified as a spike, i.e., a local valley has been found. This would eliminate false spikes. The detailed steps for computing the number of spikes for a channel is described as follows.

To perform spike detection, the number of spikes ($N_{sk}$) is initialised for the processing channel k, $N_{sk}(k)=0$, and pre-processed samples.

The filtered signal (e.g., F) is obtained based on the PPFF-FwHd filter described with reference to FIGS. 4 and 5.

The zero crossings are obtained, those crossings satisfying $I_c = F_s + T_{rp} < 0$, where $T_{rp}$ is obtained by replicating the threshold $T_r$ for channel k to the same length as $F_s$.

The method 100 thereafter identifies whether or not the processing sample is a spike. For the $i^{th}$ sample, we define $C_{n1} = I_c(i) \neq I_c(i-1)$—whether or not a crossing-transition exists—and $C_{n2} = F_s(i-1) > F_s(i)$—whether or not a valley exists. If both conditions hold, i.e., $C_{n1} \& C_{n2} = 1$, $N_{sk}(k) = N_{sk}(k)+1$ the entering point (i.e. crossing of the threshold—see FIG. 7) of the edge of the spike is found. A spike is thus detected.

This process is reiterated until all the samples are processed, and then until all the channels are processed.

The spike data (e.g. firing rates) are outputted in accordance with step 110, for every time bin width (in this context, the term "bin width" may refer to the shifting time window used in the decoding process, rather than the decoding bin width used to refresh the counter used in determining the firing rate). The extracted features, e.g. the firing rate, may be used as an input to a linear decoding function/method (linear combination of the features, e.g., linear discriminant analysis) or non-linear decoding function/method (e.g., nonlinear kernel-based support vector machine, multi-layer neural network etc.) to obtain a control signal for controlling the assistive device. Recursive Kalman filtering may also be used as an effective decoder to estimate the internal state of a brain signal given the sequence of noisy observations (features). The decoding function/method may be performed, in some embodiments, by the signal processing system (e.g. system 202 of FIG. 2) or in a device in which the components of system 202 are housed (e.g. a device placed on or attached to the scalp of the subject) or may be located remotely as described with reference to FIG. 2.

The optimal parameters should be obtained based on training data. In one embodiment, the parameters are set as: C1=5, C2=0.6745, and the time bin width is set as 100 ms.

Figure 7:
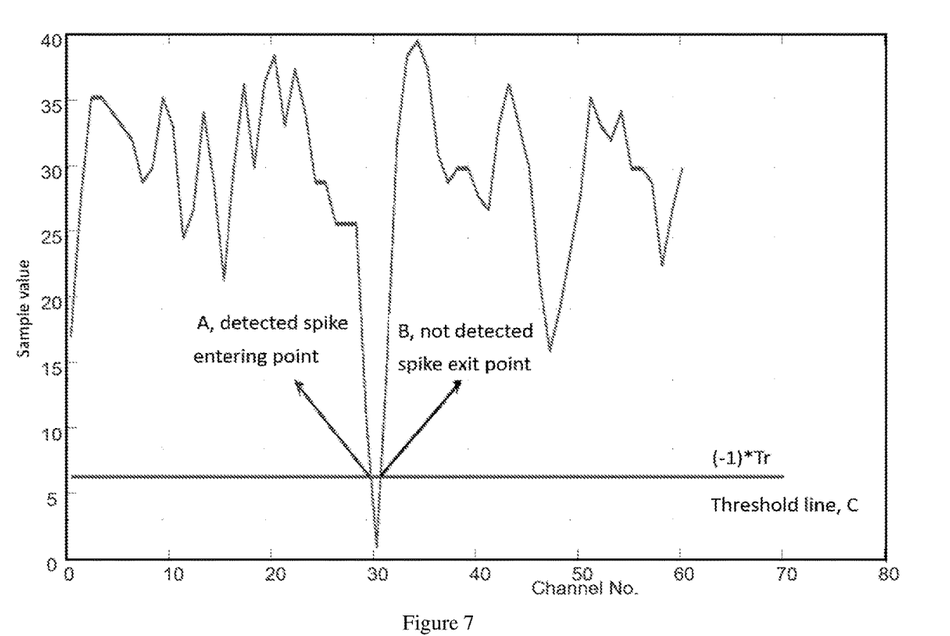
FIG. 7 illustrates spike detection in accordance with method 100.

FIG. 7 illustrates the detected entering point of the spike, point A. Point B was not detected since condition $C_{n2}$ was not satisfied. Thus, only the inward crossing of the threshold C, commencing a valley or trough, is identified.

Decoding Spike Data

Lastly, shown in FIG. 2 is a remote system (spike decoding system) 212. The remote system 212 includes a receiver with either a wired connection to signal processing system 202, or in wireless communication with signal processing system 202. The remote system 212 receives the spike data generated at step 110, and decodes that spike data using any appropriate method. Accordingly, the method 100 may further comprise decoding the spike data to determine a control command—the decoding will occur in remote system 212 in the present embodiment.

Experimental Evaluation

Experiments were conducted to validate the effectiveness of the proposed signal processing, i.e., filter-thresholding-spike detection, for fixed-point DSP implementation in BMI decoding. The results were compared with that obtained using floating point in terms of filtered data, thresholds, number of spikes and accuracies in decoding.

Data Set

All procedures and experiments were performed in compliance with the Institutional Animal Care and Use Committee (IACUC). The data set employed was obtained by training a non-human primate (NHP) to drive a mobile robot to move forward, turn left or right, or stay still using a joystick for each single trial, cued by a liquid reward from the trainer. A reward was given for the successfully performed task within 15 seconds. Three floating microwire arrays with 96 channels were used to acquire the spike signals at the left primary motor cortex, with sampling rate of 12,987 Hz. The analog joystick signals were recorded, where four classes representing the right, left and forward movements, and stop actions were defined with appropriate voltage thresholds. Data were collected on 9 non-consecutive days spanning 3 months, with each session consisting of about 20 trials for each class.

Comparison of the Filtered Data and Thresholds Obtained

Figure 8:
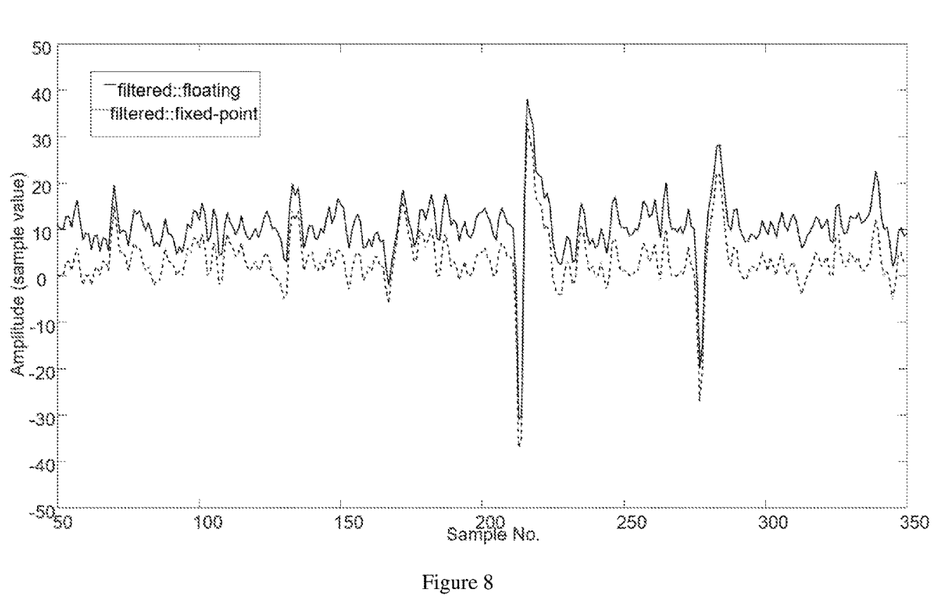
FIGS. 8 and 9 show comparisons of the filtered data of a channel and thresholds obtained.

Firstly, a comparison was made between the filtered data and thresholds obtained based on the floating-point and the present signal processing engine based on fixed-point implementation, with the filtered data for a short time segment and thresholds shown in FIG. 8—the solid line represents the filtered signal using a floating point method, and the dashed line represents the filtered signal using the proposed fixed point method. Note that the median threshold were employed in the floating-point implementation. The evaluation was based on one selected channel with prominent spikes and a time segment of 0.5 second was employed for threshold calculation.

Figure 9:
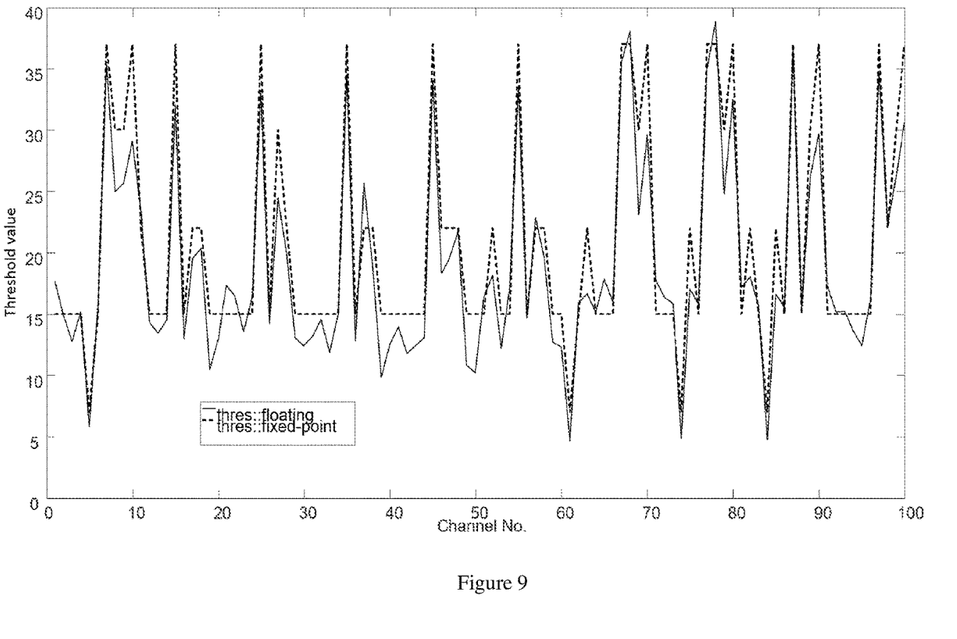

FIG. 9 shows the comparison of threshold obtained using the floating point method (solid line) and presently proposed fixed point method (broken line).

It can be seen from FIGS. 8 and 9 that the obtained filtered data and thresholds using proposed signal processing engine for fixed-point implementation match closely with that obtained using floating point implementation. This validates the effectiveness of the proposed method.

Comparison of Classification Accuracies

Table III compares the results of the accuracy of classifying the four-class data by using a floating-point processing engine and the presently described signal processing engine for fixed-point implementation—the results are for 1 NHP across 3 months for 9 non-consecutive days. In each row of Table III, the accuracy was the mean and standard error of all the accuracies of different sessions for that particular day. The last row is the mean accuracies across all the sessions over all days.

TABLE III

Accuracies (%) obtained using floating-point and proposed digital signal processing engine for fixed-point implementation.

| Experiment day | Avg. Acc across sessions of a day (mean ± standard error) | |
|---|---|---|
| | floating-point | Proposed fixed-point |
| 1 | 87.83 ± 1.00 | 77.08 ± 2.66 |
| 2 | 91.90 ± 2.27 | 90.31 ± 3.12 |
| 3 | 87.62 ± 1.94 | 87.05 ± 0.73 |
| 4 | 94.36 ± 1.55 | 84.40 ± 6.53 |
| 5 | 91.51 ± 1.70 | 80.68 ± 5.89 |
| 6 | 82.12 ± 3.63 | 70.86 ± 6.91 |
| 7 | 78.44 ± 2.19 | 87.07 ± 1.58 |
| 8 | 87.31 ± 2.91 | 87.57 ± 0.90 |
| 9 | 80.28 ± 5.39 | 81.08 ± 3.62 |
| Overall Avg. Acc. | 86.82 ± 1.83 | 82.90 ± 2.04 |

It can be observed from Table III that the proposed signal processing engine based on fixed-point implementation (presently for a signal processing system in a DSP chip implementation) yielded comparable classification accuracies compared with that of a floating-point implementation. Statistically paired t-test at 5% significance demonstrated no significant differences between the accuracies across all of the days based on the floating-point and proposed signal processing engine (p-value: 0.1343). These results revealed that the accuracies obtained for two settings were not significantly different from each other, which validated the effectiveness of the presently proposed method.

Table III shows:

Data. An NHP to drive a mobile robot to move forward, turn left or right, or stay still using a joystick.

Spike signals acquired at the left primary motor cortex, with sampling rate of 12,987 Hz. Data collected on 9 non-consecutive days spanning 3 months, each session consisted of about 20 trials for each class.

Exemplary methods that use neural activity to decode movement planning and execution for control the prosthetic devices will generally focus on the robustness of the decoding algorithms across days and sessions, as well as the decoding accuracy.

A combination of plan and peri-movement signals may be employed to improve the reconstruction of end-point movements. This is especially useful in the situation where pre-selecting the type of neural activity was not possible. Adaptive point-process filtering and maximum likelihood filtering may be employed in an estimator for plan (movement goal variable) and peri-movement signals (movement execution variable). The system may also be a closed loop system—e.g. a closed loop BMI system—that decodes the neural signal from the brain, in a known manner, to control an external actuator of system 200 to provide sensory feedback. However, this will usually be performed in remote system 212 since providing decoding functions in a signal processing system as described herein would result in higher power consumption—this is particularly important for on-chip implementations.

Mental states may be coded based on, for example, reinforcement learning, Kalman filtering, and the transition between different brain states. Functional mapping between the mental states and behaviour in view of the feedback may be learned via reinforcement learning i.e., to learn both the association between the states and control actions by the machine/system 212 and the relationship between brain activity and BMI control by the user. The system 200 may employ a neural network comprising a gamma structure front-end with time-varying gamma weight kernels, and a greedy policy backend. Rewards may also be used to update functional mapping. In general, the user will not be aware of which control actions to take, but must discover which control action yields the greatest reward.

In the decoder in system 200 (particularly remote system 212), Kalman filtering was explored for continuous decoding of the neural signal (e.g. spike data, such as firing rate and/or time of sample, outputted at step 112), in which control of a prosthetic device was achieved using intention estimating kinematics of original and modified BMIs. Velocities were modelled using the Kalman filter, where the velocity and position kinematics were encoded as intentions and feedback, respectively. The modified BMI was performed by changing the direction of velocity vectors towards an end target of the executed movements of the prosthetic device.

In order to improve the speed and robustness, the neural signals associated with direction and speed of movement were separated by the decoder and different weights were assigned. The first method is to fit the BMI (being a system incorporating the signal processing system, or the method employed by that system, depending on context) against a subject's (experimentally, the subject was a monkey) intended cursor kinematics, which is achieved by rotating the original cursor movement velocity vectors towards the target. In the second method, the velocity is modelled as the user intention and position as the feedback. This second method allows the subject to control velocity of the cursor with a measured neural signal while taking into account the influence of the current cursor position.

Parallel control of a continuous and a discrete action state decoders may be used to enable decoding of both task-related and discrete action states. A continuous decoder may be based on kinematics of the prosthetic device represented by neural signals from the motor cortex as processed by signal processing system 202. A discrete decoder is used to learn distributions and transitions among different states related to task, velocity of prosthetic device and engagement of user or subject. Internal dynamics of the neural activity was modelled by the neural dynamical structure and was incorporated into the control to restore the motor function. The estimated neural state was a linear combination of the dynamical evolution of previous neural state estimate, and newly observed spike counts in the spike data.

In order to increase the performance and robustness of BMI, two decoders were proposed, where the first decoder was for intention execution, and the second decoder was for error detection in a close-loop error fashion. The rationale lies in the assumption that neural correlates of BMI-based behavior errors exist in some brain regions, e.g., the motor cortex such as the dorsal premotor cortex or primary motor cortex. The error detection could detect, prevent and correct the errors and free the user or subject from manual correction.

The reference to any prior art in this specification is not, and should not be taken as, an acknowledgment or any form of suggestion that the prior art forms part of the common general knowledge.

In this specification and the statements made herein, unless stated otherwise, the word "comprise" and its variations, such as "comprises" and "comprising", imply the inclusion of a stated integer, step, or group of integers or steps, but not the exclusion of any other integer or step or group of integers or steps.

References in this specification to any prior publication, information derived from any said prior publication, or any known matter are not and should not be taken as an acknowledgement, admission or suggestion that said prior publication, or any information derived from this prior publication or known matter forms part of the common general knowledge in the field of endeavour to which the specification relates.

The invention claimed is:

1. A signal processing method on a signal processing system in a brain machine interface (BMI), comprising the processing steps of:
   receiving input data comprising cortical signal samples;
   applying a filter to the input data to obtain filtered data samples;
   calculating a threshold by:
      initializing one or more parameters;
      recursively updating the one or more parameters based on a value of each filtered data sample;
      grouping each filtered data sample into an ordered set of groups, based on the value of the respective filtered data sample and the recursively updated one or more parameters;
      identifying a threshold group based on a number of filtered data samples grouped into groups distributed, around the threshold group, in the ordered set of groups; and
      determining the threshold based on the threshold group and the one or more parameters;
   identifying a spike in each of one or more subsequently received data samples based on the threshold; and
   outputting spike data corresponding to the spike or spikes identified in the one or more subsequently received data samples.

2. The method according to claim 1, wherein the input data is measured by a sensor in a cortex of a patient.

3. The method according to claim 2, wherein the sensor is an implanted multi-channel sensor array, the signal processing system is connected to the implanted multi-channel sensor array and the processing steps are performed on cortical signal samples captured on each respective channel of the multi-channel sensor array.

4. The method according to claim 3, wherein recursively updating the one or more parameters based on a value of each filtered data sample comprises setting at least one of iMax and iMin to be, respectively, a maximum value and a minimum value across all of the filtered data samples.

5. The method according to claim 1, wherein initializing the one or more parameters comprises setting:
   a maximum value (iMax);
   a minimum value (iMin); and
   a number of groups for the ordered set of groups.

6. The method according to claim 5, further comprising calculating a dynamic range of the filtered data samples (iRng) based on the formula:

$$iRng = iMax - iMin + 1$$

7. The method according to claim 6, wherein grouping each filtered data sample into an ordered set of groups comprises identifying, for each filtered data sample, a respective group of the ordered set of groups according to the formula:

$$iB = \frac{x(k) - iMin}{iRng} \times nBin$$

wherein iB is the bin index for the respective group, x(k) is a filtered data sample comprising k seconds of the input data, and nBin is the number of groups in the ordered set of groups.

8. The method according to claim 1, wherein applying a filter to the input data to obtain filtered data samples comprises applying a Finite Impulse Response (FIR) filter or an Infinite Impulse Response (IIR) filter to the input data.

9. The method according to claim 8, wherein applying a filter to the input data to obtain filtered data samples comprises applying an IIR filter, and wherein the input data has a first precision in which the cortical signal samples are each represented by a first number of bits, and wherein applying an IIR filter to the input data comprises applying a modified Direct Form I filter of order N, having 2N delay units, involving:
  scaling upscaling filter coefficients b and scaling downscaling filter coefficients a to obtain scaled filter coefficients $\tilde{b}$ and $\tilde{a}$ respectively;
  casting an input signal x(n) and the scaled filter coefficients into a second precision, wherein x(n) comprises the input data and the second precision is higher than the first precision;
  applying the IIR filter to the input signal x(n), using $\tilde{b}$ and $\tilde{a}$ as coefficients for the IIR filter, to obtain an intermediate result; and
  downscaling the intermediate result into the first precision.

10. The method according to claim 9, wherein scaling upscaling filter coefficients b and scaling downscaling filter coefficients a to obtain scaled filter coefficients $\tilde{b}$ and $\tilde{a}$ comprises:
  applying the IIR filter to a stored set of cortical signal samples to produce a first set of filtered samples;
  applying a floating-point filter to the stored set of cortical signal samples to produce a second set of filtered samples;
  determining a number of precision bits $n_p$ resulting in a minimal difference between the first set of filtered samples and the second set of filtered samples, and
  scaling to $2^{n_p}$ to obtain the scaled filter coefficients b and $\tilde{a}$.

11. The method according to claim 9, wherein the intermediate result has a first form y(n) and a second form, and wherein applying the IIR filter to the input signal x(n), using $\tilde{b}$ and $\tilde{a}$ as coefficients for the IIR filter, obtains y(n), the method further comprising:
  obtaining the second form of the intermediate result by retaining a sign S of y(n), casting y(n) to an unsigned integer format,
  wherein downscaling the intermediate result into the first precision comprises downscaling the second form of the intermediate result into the first precision.

12. The method according to claim 11, wherein the second form is $SY_f$, which is obtained from y(n) by:
  retaining the sign S of y(n);
  casting y(n) to an unsigned integer format $Y_f$; and
  bit-shifting $Y_f$ to obtain $SY_f$.

13. A signal processing system for a brain machine interface (BMI), the signal processing system comprising:
  a receiver for receiving cortical signals measured by a multi-channel sensor array;
  a wireless transmitter for transmitting an output;
  memory; and
  at least one processor, the memory storing instructions that, when executed by the at least one processor, cause the at least one processor to, for each channel of the multi-channel sensor array:
  receive input data at the receiver, the input data comprising cortical signal samples;
  apply a filter to the input data to obtain filtered data samples;
  calculate a threshold by:
    initializing one or more parameters;
    recursively updating the one or more parameters based on a value of each filtered data sample;
    grouping each filtered data sample into an ordered set of groups, based on the value of the respective filtered data sample and the recursively updated one or more parameters;
    identifying a threshold group based on a number of filtered data samples grouped into groups distributed, around the threshold group, in the ordered set of groups; and
    determining the threshold based on the threshold group and the one or more parameters; and
  identify a spike in each of one or more subsequently received data samples, received at the receiver, based on the threshold,
  the instructions, when executed by the at least one processor, further causing the at least one processor to output the output, from the wireless transmitter to a remote system, the output comprising spike data corresponding to the spike or spikes identified in the one or more subsequently received data samples.

14. The signal processing system according to claim 13, wherein the at least one processor is caused to apply a filter to the input data to obtain filtered data samples by applying a Finite Impulse Response (FIR) filter or an Infinite Impulse Response (IIR) filter to the input data.

15. The signal processing system according to claim 14, wherein applying a filter to the input data to obtain filtered data samples comprises applying an IIR filter, and wherein the input data has a first precision in which the cortical signal samples are each represented by a first number of bits, and the at least one processor is caused to apply an IIR filter to the input data by applying a modified Direct Form I filter of order N, having 2N delay units, by:
  scaling upscaling filter coefficients b and scaling downscaling filter coefficients a to obtain scaled filter coefficients $\tilde{b}$ and $\tilde{a}$ respectively;
  casting an input signal x(n) and the scaled filter coefficients into a second precision, wherein x(n) comprises the input data and the second precision is higher than the first precision;
  applying the IIR filter to the input signal x(n), using $\tilde{b}$ and $\tilde{a}$ as coefficients for the IIR filter, to obtain an intermediate result; and
  downscaling the intermediate result into the first precision.

16. The signal processing system according to claim 15, wherein the at least one processor is caused to scale upscaling filter coefficients b and scale downscaling filter coefficients a to obtain scaled filter coefficients $\tilde{b}$ and $\tilde{a}$ by:
  applying the IIR filter to a stored set of cortical signal samples to produce a first set of filtered samples;
  applying a floating-point filter to the stored set of cortical signal samples to produce a second set of filtered samples;
  determining a number of precision bits $n_p$ resulting in a minimal difference between the first set of filtered samples and the second set of filtered samples, and scaling to $2^{n_p}$ to obtain the scaled filter coefficients $\tilde{b}$ and $\tilde{a}$.

17. The signal processing system according to claim 15, wherein the intermediate result has a first form y(n) and a second form, and wherein the at least one processor is caused to:
  apply the IIR filter to the input signal x(n), using $\tilde{b}$ and $\tilde{a}$ as coefficients for the IIR filter, to obtain y(n); and
  obtain the second form of the intermediate result by retaining a sign S of y(n), casting y(n) to an unsigned integer format,
  wherein downscaling the intermediate result into the first precision comprises downscaling the second form of the intermediate result into the first precision.

18. The signal processing system according to claim 17, wherein the second form is $SY_f$, and the at least one processor obtains $SY_f$ from y(n) by:
  retaining the sign S of y(n);
  casting y(n) to an unsigned integer format $Y_f$; and
  bit-shifting $Y_f$ to obtain $SY_f$.

19. The signal processing system according to claim 18, wherein the at least one processor is caused to bit-shift $Y_f$ by left shifting $Y_f$ to scale by $2^{n_r-n_p}$, wherein $n_r$ is a total number of bits used to represent x(n).

20. A brain machine interface comprising the signal processing system according to claim 13.

* * * * *